(12) United States Patent
Menter

(10) Patent No.: US 11,642,327 B2
(45) Date of Patent: May 9, 2023

(54) CREATINE NUTRITIONAL SUPPLEMENT

(71) Applicant: Dylan Robert Menter, Los Angeles, CA (US)

(72) Inventor: Dylan Robert Menter, Los Angeles, CA (US)

( * ) Notice: Subject to any disclaimer, the term of this patent is extended or adjusted under 35 U.S.C. 154(b) by 151 days.

(21) Appl. No.: 17/221,787

(22) Filed: Apr. 3, 2021

(65) Prior Publication Data

US 2022/0054442 A1 Feb. 24, 2022

Related U.S. Application Data

(60) Provisional application No. 63/069,650, filed on Aug. 24, 2020.

(51) Int. Cl.
| | | |
|---|---|---|
| A61K 36/45 | (2006.01) |
| A61K 31/198 | (2006.01) |
| A61K 47/26 | (2006.01) |
| A61K 47/12 | (2006.01) |
| A61K 35/748 | (2015.01) |
| A23L 33/105 | (2016.01) |
| A23L 33/125 | (2016.01) |
| A23L 17/60 | (2016.01) |
| A23L 29/231 | (2016.01) |
| A23L 29/00 | (2016.01) |
| A23L 33/175 | (2016.01) |
| A23G 3/44 | (2006.01) |
| A23G 3/42 | (2006.01) |
| A23G 3/48 | (2006.01) |
| A23G 3/36 | (2006.01) |
| A61K 9/00 | (2006.01) |

(52) U.S. Cl.
CPC ............ *A61K 31/198* (2013.01); *A23G 3/366* (2013.01); *A23G 3/42* (2013.01); *A23G 3/44* (2013.01); *A23G 3/48* (2013.01); *A23L 17/60* (2016.08); *A23L 29/035* (2016.08); *A23L 29/231* (2016.08); *A23L 33/105* (2016.08); *A23L 33/125* (2016.08); *A23L 33/175* (2016.08); *A61K 9/0056* (2013.01); *A61K 35/748* (2013.01); *A61K 36/45* (2013.01); *A61K 47/12* (2013.01); *A61K 47/26* (2013.01); *A23V 2002/00* (2013.01)

(58) Field of Classification Search
None
See application file for complete search history.

(56) References Cited

U.S. PATENT DOCUMENTS

2021/0228483 A1* 7/2021 Wan ....................... A61K 36/74

* cited by examiner

Primary Examiner — Russell G Fiebig
(74) Attorney, Agent, or Firm — Plager Schack LLP; Mark H. Plager; Naomi Mann

(57) ABSTRACT

Disclosed herein is a nutritional supplement containing creatine, including compositions, formulations, and combinations of ingredients in the creatine nutritional supplement, as well as processes for manufacturing these supplements. The disclosed nutritional supplement can include creatine, a gelling agent such as pectin or gelatin, an oligosaccharide, a disaccharide, and water.

15 Claims, 1 Drawing Sheet

CREATINE NUTRITIONAL SUPPLEMENT

PRIORITY

This application claims priority to and the benefit under 35 U.S.C .sctn. 119(e) of U.S. Provisional Patent Application Ser. No. 63/069,650, filed Aug. 24, 2020. The foregoing applications are incorporated herein by reference in their entireties.

FIELD

This application relates generally to a creatine nutritional supplement, including compositions, formulations, and combinations of ingredients in the creatine nutritional supplement, as well as processes for manufacturing embodiments of such supplements.

BACKGROUND

Ranked as one of the healthiest amino acids found in seafood and red meat, synthetically made creatine supplements that's also naturally produced in the human body. Creatine is produced in the human body from the amino acids glycine and arginine, with an additional requirement for methionine to catalyze the transformation of guanidinoacetate to creatine. There are many known benefits of creatine, including but not limited to, increasing strength, focus, short-term memory, and energy, boosting the immune system, fighting age-degenerative diseases, and slowing the signs of aging. Creatine has also been known to assist in muscle growth.

However, the relatively low-level of dissolvability and unpleasant taste makes it difficult to consume in water-soluble powder form. Other consumables and nutritional supplements that incorporate creatine have failed to solve the problems associated with creatine intake, including eliminating the unpleasant tastes and low-level of dissolubility associated with creatine.

Therefore, what is needed is an improved nutritional supplement that includes a specifically-developed composition of ingredients, including creatine, that reduces significantly or eliminates the unpleasant creatine taste and insoluble characteristics.

SUMMARY

Disclosed herein is a food product, which can include creatine at about 6% to 35% by weight, pectin, an oligosaccharide, a disaccharide at about 25% to 70% by weight, and water. In some embodiments, the disaccharide is by weight between about 30% and 60% or about 35% and 50%. In some embodiments, the creatine is by weight is between about 7% and 30%, about 8% and 25%, or about 12% and 13%. In some embodiments, the pectin is by weight between about 1% and 20%, or about 1.75% and 7%. In some embodiments, the oligosaccharide is by weight between trace amounts and about 65%, about 25% and 55%, or about 30% and 50%.

In some embodiments, the food product can include an acidifying agent and a buffer agent. The acidifying agent can be by weight between trace amounts and about 10%, or about 0.3% to 2.5%. The buffer agent can be by weight between trace amounts and about 3%, or about 0.2% and 1.5%. In some embodiments, the acidifying agent can be selected from the group consisting of lactic acid, formic acid, citric acid, malic acid, tartaric acid, and a combination thereof. The buffer agent can be selected from the group consisting of sodium citrate, magnesium citrate, potassium citrate, zinc citrate, protein, amino acid, and a combination thereof. In some embodiments, the food product can include a natural flavor, the natural flavor can be a volatile substance such as ethanol.

In some embodiments, in the food product disclosed herein by weight percentages, the creatine can be between about 6% and 20%, the pectin can be between about 1.75% and 7%, the oligosaccharide can be between about 30% and 47.5%, the disaccharide can be between about 35% and 50%, and the water can be between about 5% and 16%. In some embodiments, in the food product disclosed herein by weight percentages, the creatine can be about 12.5%, the pectin can be between about 8% and 20%, the oligosaccharide can be between about 10% and 40%, the disaccharide can be between about 35% and 65%, and the water can be between about 2% and 5%.

In some embodiments of the food product disclosed herein, the oligosaccharide can be tapioca and the disaccharide can be cane sugar. The food product can include by weight sodium citrate between about 0.01% and 0.03%; citric acid between about 6% to 10%; malic acid between about 3% and 8%; a natural flavor between about 0.1% and 0.3%; spirulina between about 0.01% and 0.2%; organic blueberry between about 0.01% and 0.2.

In some embodiments, the food product can include creatine, gelatin, an oligosaccharide, a disaccharide at about 25% to 70% by weight, and water. In some embodiments, the creatine can be between about 5% to 20%, the gelatin can be between about 3% to 20%, and the water can be between about 5% to 20%.

Further disclosed herein is a method of producing the food product, which can include hydrating pectin with water under heat, solubilizing a disaccharide and an oligosaccharide, forming a mixture of the hydrated pectin and the solubilized disaccharide and oligosaccharide, adding a buffer agent to the mixture, adding creatine to the mixture, adding a natural flavor to the mixture, adding an acidifying agent to the mixture, cooking the mixture between about 85 to 115 Celsius for about 5 to 60 minutes, holding the mixture between about 90 to 100 Celsius for about 5 to 30 minutes, and depositing the mixture into a mold.

BRIEF DESCRIPTION OF DRAWINGS

In order to facilitate a full understanding of the present disclosure, reference is now made to the accompanying drawings, in which like elements are referenced with like numerals. These drawings should not be construed as limiting the present disclosure but are intended to be illustrative only. The drawings are not necessarily to scale, or inclusive of all elements of a system, emphasis instead generally being placed upon illustrating the concepts, structures, and techniques sought to be protected herein.

DESCRIPTION

Figures 1, 2:
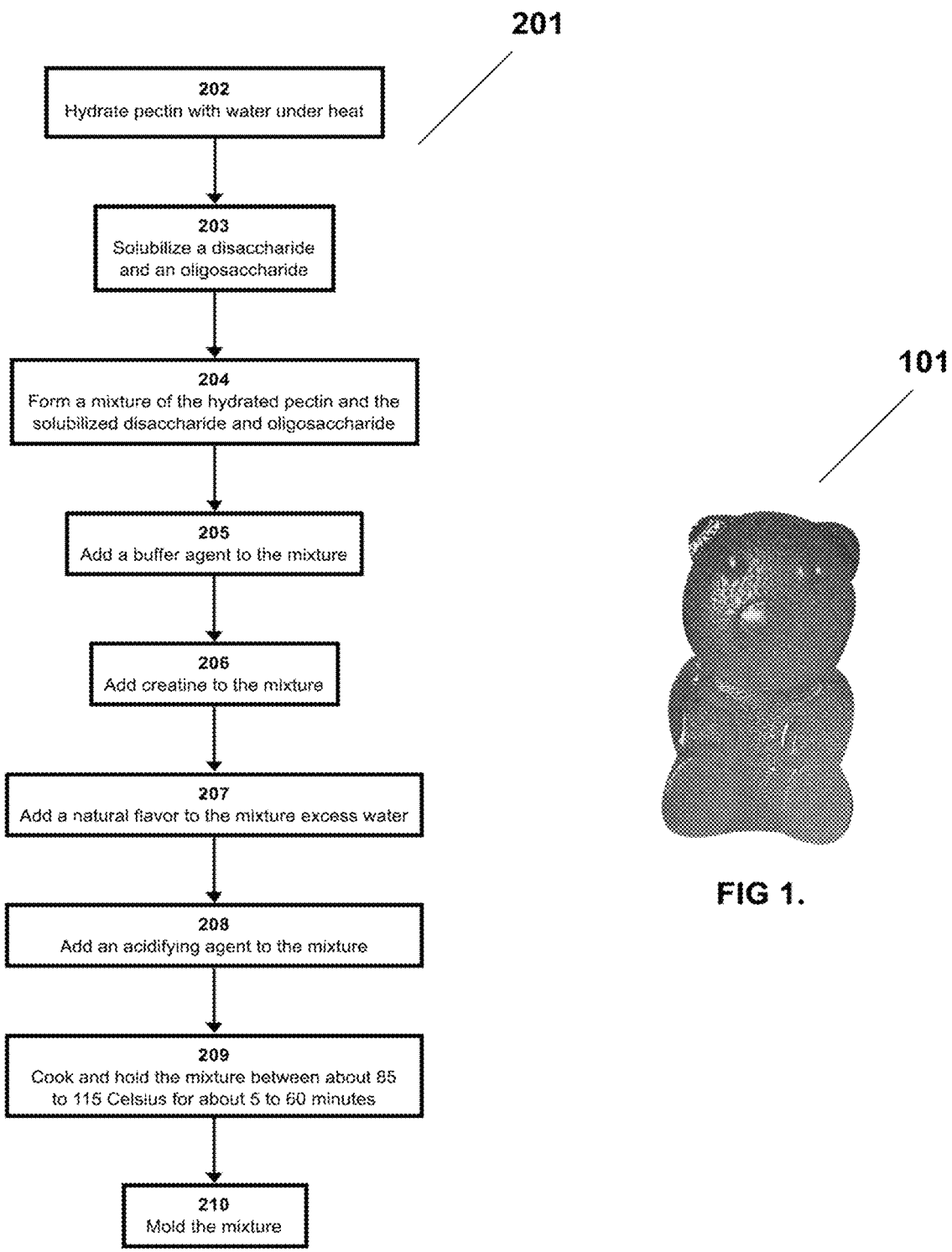
FIG. 1 depicts an creatine gummy design of the nutrition supplement, according to some embodiments of the present disclosure.
FIG. 2 shows a flowchart illustrating the manufacturing process of a nutrition supplement, according to some embodiments of the present disclosure.

The nutritional supplement described herein delivers all the age-old traditional benefits of creatine packed into a pleasant and delicious tasting gummy, gelatin, or other product, that may also be infused with super foods and vitamins. Embodiments of the present disclosure described herein effectively mask the flavor of creatine, making the gummy (or other forms, as mentioned later on) much more appealing to consumers.

The current disclosure also describes embodiments that mask the unpleasant taste of creatine without the use of excessive levels of sugar. For example, the use of an amount of sugar that exceeds the solubility point can cause undesirable crystallization and hardening of the supplement. Moreover, excessive sugar can be undesirable for consumers with a goal of minimizing their daily sugar intake for health purposes.

Any discussion of numerical values or ranges such as weight percentages and pH values can be understood as referring to the exact values and also reasonable approximations of those values/ranges as would be understood to a person of ordinary skill in the art.

In some embodiments, the nutritional supplement disclosed herein may include creatine. Some non-limiting concentrations of creatine in the nutritional supplement in weight percentages can include, but not limited to, about 0.1% to 50%, about 1% to 45%, about 5% to 40%, about 6% to 35%, about 7% to 30%, about 8% to 25%, about 9% to 20%, about 10% to 15%, about 0.1% to 30%, about 2.5% to 25%, or about 5% to 20%. In some embodiments, the concentration of the creatine can be about 2.5% to 25% by weight. In some embodiments, the concentration of the creatine can be about 5% to 20% by weight, in some embodiments, the concentration of the creatine can be about 12% to 13% by weight. In some embodiments, the concentration of the creatine can be about 12.5% by weight.

In some embodiments, the nutritional supplement disclosed herein may include an oligosaccharide. In some embodiments, the oligosaccharide can be a syrup. Exemplary syrups can include, but are not limited to, glucose syrup, com syrup, rice syrup, invert syrup, isomaltooligosaccharide (IMO) sugar, tapioca, fructooligosaccharide (FOS) syrup, starch, fiber syrup, inulin, fruit puree, fruit concentrate, high maltose syrup, agave syrup, and any combinations thereof. In some embodiments, the syrup can be a corn syrup including a dextrose equivalent (DE) of about 40 to about 70 DE. In some embodiment's embodiment, the corn syrup comprises a DE of about 55 to 62 DE. In some embodiments, the corn syrup is about 62 DE. The corn syrup can be a high fructose corn syrup. In some embodiments, tapioca can be used. Some non-limiting concentrations of syrup in the nutritional supplement in weight percentages can include, but not limited to, about 0.1% to 80%, about 5% to 75%, about 10% to 70%, about 15% to 65%, about 20% to 60%, about 25% to 55%, about 30% to 50%, about 35% to 47.5%, about 1% to 65%, about 25% to 55%, or about 30% to 47.5%. In some embodiments, the concentration of the syrup can be about 1% to 65% by weight. In some embodiments, the concentration of the syrup can be about 25% to 55% by weight. In some embodiments, the concentration of the syrup can be about 30 to 47.5% by weight.

In some embodiments, the nutritional supplement disclosed herein may include a gelling agent. Exemplary gelling agents can include, but not limited to pectin, gelatin, seaweed extract, agar, carrageenan, gum Arabic, and any combinations thereof. In some embodiments, pectin can be used as a gelling agent. In some embodiments, gelatin can be used as a gelling agent. Some non-limiting concentrations of gelling agent in the nutritional supplement in weight percentages can include, but not limited to, about 0.1% to 60%, about 0.5% to 50%, about 1% to 40%, about 1.5% to 35%, about 1.75% to 30%, about 2% to 20%, or about 5% to 7%. In some embodiments, the concentration of the gelling agent can be about 1% to 20% by weight. In some embodiments, the concentration of the gelling agent can be about 1.5% to 10% by weight. In some embodiments, the concentration of the gelling agent can be about 1.75% to 7% by weight. In some embodiments, the concentration of the gelling agent can be about 8% to 20% by weight. In some embodiments, the concentration of the gelling agent can be about 1% to 50% by weight. In some embodiments, the concentration of the gelling agent can be about 2% to 30% by weight. In some embodiments, the concentration of the gelling agent can be about 3% to 20% by weight.

In some embodiments, gelatin may be used as a gelling agent. Examples of gelatins can include but are not limited to 120 Bloom gelatin. 125 Blown gelatin, 160 Bloom gelatin, 190 Bloom gelatin. 200 Bloom gelatin, 220 Bloom gelatin. 250 Bloom gelatin, and any combinations thereof. The gelatin can be acid treated. In some embodiments, the gelatin has a bloom strength from about 80 to 250 Bloom, in some embodiments, the gelatin has a bloom strength from about 125 to 250 Bloom, in some embodiments, the gelatin has a bloom strength of about 160 to 250 Bloom. In some embodiments, the gelatin has a bloom strength of about 190 to 250 Bloom.

In some embodiments, the nutritional supplement disclosed herein can include a sweetener, in some embodiments, the sweetener can be a disaccharide. Exemplary sweeteners can include, but not limited to, non-organic cane sugar, organic cane sugar, sugar alcohol, natural sweeteners such as stevia or monk fruit, sugar alternatives such as short length carbohydrate, any of the plethora of artificial sweeteners known to one of ordinary skill in the art, and any combinations thereof. In some embodiments, organic cane sugar can be used as a sweetener. Some non-limiting concentrations of sweetener in the nutritional supplement in weight percentages can include, but not limited to, about 10% to 80%, about 15% to 75%, about 20% to 70%, about 25% to 65%, about 30% to 60%, about 35% to 55%, or about 40% to 50%. In some embodiments, the concentration of the sweetener can be about 25% to 70% by weight. In some embodiments, the concentration of the sweetener can be about 35% to 60% by weight. In some embodiments, the concentration of the sweetener can be about 42% to 50% by weight.

In some embodiments, the weight ratio between disaccharide and oligosaccharide in the disclosed nutritional supplement can be about 0.2/1 to 10/1, about 0.4/1 to 9/1, about 0.6/1 to 8/1, about 1/1 to 6/1, or about 5/1.

In some embodiments, the nutritional supplement disclosed herein can include water. Some non-limiting concentrations of water in the nutritional supplement in weight percentages can include, but not limited to, about 0.1% to 40%, about 0.5% to 30%, about 1% to 25%, about 2% to 20%, about 5% to 16%, about 7% to 13%, or about 10% to 12%. In some embodiments, the concentration of the water can be about 1% to 25% nutritional supplement. In some embodiments, the concentration of the water can be about 2% to 20% nutritional supplement. In some embodiments, the concentration of the water can be about 5% to 16% nutritional supplement. In some embodiments, the concentration of the water can be about 2% to 5% nutritional supplement. In some embodiments, the concentration of the water can be about 5% to 20% nutritional supplement.

In some embodiments, the nutritional supplement disclosed herein may include an acidifying agent. Exemplary acidifying agents can include, but not limited to lactic acid, formic acid, citric acid, malic acid, fumaric acid, tartaric acid, glucono-delta lactone, salts of gluconic acid, phosphoric acid, succinic acid, adipic acid, ascorbic acid, acetic acid, and any combinations thereof, in some embodiments, citric acid can be used as an acidifying agent. Some non-limiting concentrations of the acidifying agents in the nutritional supplement in weight percentages can include, but not limited to, from a trace amount to about 15%, about 0.1% to 10%, about 0.2% to 7%, about 0.3% to 5%, about 0.5% to 4%, about 0.7% to 3%, or about 1% to 2.5%. In some embodiments, the concentration of the acidifying agent can be from a trace amount to about 10% by weight. In some embodiments, the concentration of the acidifying agent can be about 0.2% to 5% by weight. In some embodiments, the concentration of the acidifying agent can be about 0.3% to 2.5% by weight.

In some embodiments, the nutritional supplement disclosed herein may include a buffer agent. Exemplary acidifying agents can include, but not limited to sodium citrate, magnesium citrate, trisodium citrate, bisodium citrate, any protein or amino acids, and any combinations thereof. In some embodiments, sodium citrate can be used as a buffer agent. Some non-limiting concentrations of the butler agent in the nutritional supplement in weight percentages can include, but not limited to, from trace amount to about 5%, about 0.1% to 4%, about 0.2% to 3%, about 0.3% to 2%, about 0.4% to 1%, or about 0.5% to 0.7%. In some embodiments, the concentration of the buffer agent can be from trace amount to about 10% by weight. In some embodiments, the concentration of the buffer agent can be about 0.1% to 2% by weight. In some embodiments, the concentration of the buffer agent can be about 0.2% to 1.5% by weight.

In some embodiments, the nutritional supplement disclosed herein may include a flavorant. Exemplary flavorants can include oils including but not limited to spearmint oil, peppermint oil, cinnamon oil, oil of wintergreen (methylsalicylate), clove oil, bay oil, anise oil, eucalyptus oil, thyme oil, cedar leaf oil, oil of nutmeg, oil of sage, oil of bitter almonds, cassia oil, and any combinations thereof. The flavorants can include artificial, natural or synthetic fruit flavors such as citrus or fruit oils and/or essences including apple, apricot, banana, blueberry, cherry, grape, grapefruit, kiwi, lemon, lime, orange, pear, peach, pineapple, plum, raspberry, strawberry, tangerine and watermelon. Mixtures of the aforementioned flavors are possible. In some embodiments, the concentrations of the flavorants in weight percentages can be from trace amount to about 0.6%, about 0.1% to 0.5%, about 0.2% to 0.4%, or about 0.15% to 0.35%.

Additional flavorants may include, but are not limited to menthol, artificial vanilla, cinnamon derivatives, and various fruit flavors, whether employed individually or in admixture. Flavorings can also include, for example, aldehydes and esters including cinnamyl acetate, cinnamaldehyde, citral diethylacetal, dihydrocarvyl acetate, eugenyl formate, p-methylamisol, acetaldehyde (apple); benzaldehyde (cherry, almond), anisic aldehyde (licorice, anise); cinnamic aldehyde (cinnamon); citral, i.e., alpha citral (lemon, lime); ethyl vanillin (vanilla, cream); hellotropine, i.e., piperonal (vanilla, cream); vanillin (vanilla, cream); alpha-amyl cinnamaldehyde (spicy fruity flavors); butyraldehyde (butter, cheese); valcraldehyde (butter, cheese): citronellal; decannal (citrus fruits); CA 02864531 2014-09-19 aldehyde C-8 (citrus fruits); aldehyde C-9 (citrus fruits); aldehyde C-12 (citrus fruits); 2-ethylbutyraldehyde (berry fruits); tolyl aldehyde (cherry, almond); veratraldehyde (vanilla); 2,6-dimethyl-5-heptenal, i.e., melonal (melon); 2,6-dimethyloctanal (green fruit); and 2-dodecenal (citrus, mandarin), mixtures thereof and the like. Additional flavor compounds include ethylacetate, thiophene, ethylpropionate, ethyl bulyrate, 2-hexanoate. 2-methylpyazine, heptaldehyde, 2-octanone, limonene, and eugenol.

In some embodiments, a natural flavor is used for the disclosed nutritional supplement food product. The natural flavor may include a volatile substance which can be easily evaporated at ambient pressure and temperature, in some embodiments, the volatile substance in the natural flavor may be an alcohol such as ethanol.

In some embodiments, the nutritional supplement disclosed herein may include a colorant. Exemplary colorants can include natural or uncertified colors from natural sources or certified colors for the effect of color. In some embodiments, the colorant can include dyes, certified aluminum lakes or colors derived from a natural source. The colorant may be water-based, oil-based of dry. The colorants can be primary colors, blends of colors or discrete mixtures of colors, such as confetti. The concentrations of the colorant in the nutritional supplement in weight percentages can be from trace amount to about 0.6%, about 0.1% to 0.5%, about 0.2% to 0.4%, or about 0.15% to 0.35%.

In some embodiments, the nutritional supplement disclosed herein may include vitamins. Examples of vitamins can include, but are not limited to vitamin E, vitamin C, vitamin B2, vitamin B3, and vitamin B6, vitamin B9, and any combinations thereof, in some embodiments, the nutritional supplement can include vitamin B9 from trace amount to about 0.10%, about 0.001% to 0.05%, about 0.002% to 0.01%, or about 0.003% to 0.005% by weight. In some embodiments, the concentration of vitamin B9 is about 0.003% by weight. For a serving of about 4 g gummy, the amount of B9 can be about a trace amount to 5,000 microgram (.mu.g), about 1 .mu.g to 3.000 .mu.g, about 5 .mu.g to 1,500 mu.g, about 10 .mu.g to 900 .mu.g, about 50 mu.g to 800 .mu.g, about 1 .mu.g to 800 .mu.g, or about 50 .mu.g to 1,000 .mu.g. In some embodiments, the nutritional supplement can include vitamin B12 from trace amount to about 0.10%, about 0.00001% to 0.05%, about 0.00002% to 0.01%, or about 0.00003% to 0.005% by weight. In some embodiments, the concentration of vitamin B12 is about 0.00003% by weight. For a serving of about 4 g gummy, the amount of B12 can be about trace amount to 100 .mu.g, about 0.1 .mu.g to 50 .mu.g, about 0.12 .mu.g to 38.4 .mu.g, about 0.24 .mu.g to 19.2 .mu.g, about 0.6 .mu.g to 9.6 .mu.g, about 0.12 .mu.g to 9.6 .mu.g, or about 0.6 .mu.g to 38.4 .mu.g.

In some embodiments, the nutritional supplement can include amino acids, which can include, but are not limited to histidine, isoleucine, leucine, lysine, methionine, phenylalamine, threonine, tryptophan, valine, alanine, arginine, asparagine, aspartic acid, cysteine, glutamic acid, glutamine, glycine, ornithine, proline, selenocysteine, serine, tyrosine, and combinations thereof. In some embodiments, the nutritional supplement can include about 0.05% to 10% amino acids by weight.

In some embodiments, the nutritional supplement can optionally include an emulsifier. Some non-limiting examples of emulsifiers can include, but are not limited to sucrose esters, soy lecithin, sunflower lecithin, egg lecithin, lecithins and combinations thereof. In some embodiments, the nutritional supplement can include an emulsifier in weight percentages from trace amount to about 1%, about 0.2% to 0.8%, trace amount to about 0.5%, about 0.5% to 1%, about 0.3% to 0.6%, or about 0.1% to 0.5%.

In some embodiments, the nutritional supplement of the present disclosure can optionally be coated with a wax and/or oil. Some non-limiting examples of suitable wax can include, but are not limited to carnauba wax, bees wax, and the like. Sone non-limiting examples of suitable oils can include, but are not limited to, mineral oil, coconut oil, vegetable oil, and the like. The nutritional supplement of the present disclosure can further be coated with a flavorant, such as sugar granules or flavor particles.

Various other ingredients in the disclosed nutritional supplement that may be used include, but are not limited to, herbal additives, ascorbic acid, cocoa powder to create chocolate, cocoa butter, palm kernel oil, sunflower lecithin, or soy lecithin. In some embodiments, the nutritional supplement may also include cannabidiol (CBD), ginger, tetrahydrocannabinol (THC), pepper, chili, cayenne, turmeric, collagen, buteric acid, salts or esters of beta-hydroxybutyric acid (BHB), or any combinations thereof. In some embodiments, the nutritional supplement can include spirulina, organic blueberry, or any combinations thereof.

FIG. 1 depicts an exemplary gummy design 101 as used in the creatine nutritional supplement, according to some embodiment of the present disclosure. The creatine nutritional supplement of this disclosure may take many other forms, including, but not limited to, chewables, worms, caramel steering, hard candy, or chocolate. In some embodiments, the creatine nutritional supplement can include by weight about 10% to 30% organic tapioca, about 2% to 5% water, about 45% to 65% organic cane sugar, about 12.5% creatine, about 8% to 20% pectin, about 0.01% to 0.03% sodium citrate, about 6% to 10% citric acid, about 3% to 8% malic acid, about 0.1 to 0.3% natural flavor, about 0.01% to 0.2% spirulina, about 0.01% to 0.2% organic blueberry.

FIG. 2 depicts an exemplary process 201 for manufacturing creatine nutritional supplements with a strongly mitigated or masked creatine tastes, according to some embodiments of the present disclosure. The process starts at step 202 to hydrate a gelling agent such as a pectin with water at an elevated temperature of about 90 to 100 Celsius and pH value of about 4.2 to 5.6. Then at step 203, a disaccharide and an oligosaccharide are solubilized. Step 204 forms a mixture of the hydrated pectin and the solubilized disaccharide and oligosaccharide. At step 205, a buffer agent is added to the mixture to maintain the mixture at a pH value of about 4.2 to 5.6. At step 206, creatine is added. At step 207, a natural flavor is added into the mixture. At step 208, an acidifying agent is added to the mixture at an elevated temperature of about 80 to 110 Celsius and a pH value of about 2.8 to 3.7. At the next step 209, the mixture is cooked and held between about 85 to 115 Celsius for about 5 to 60 minutes. The temperature range for the cooking step 209 may vary with the specific gelling agent used, some of which is generally known to one of ordinary skill in the art. For example, if agar, gelatin, or starch is used, the temperature in some embodiments may be between 30 and 90 degrees Celsius. And for example, if the gelling agent is carrageenan, the temperature in some embodiments may be between 50 and 150 degrees Celsius. The mixture is then deposited into a starch tray or silicone mold at step 210. Once this has been done, the mixtures may undergo drying. Finally, the mixture may be packaged for distribution. Throughout the process, in some embodiments, various other properties must be kept within certain ranges.

The pH levels in some embodiments can have desired ranges, but these can vary with the gelling agent. If gelatin, pectin, or carrageenan are used, the pH in some embodiments can be kept between about 2 and 6. If agar is used, the pH in some embodiments can be kept between about 3 and 8. In some embodiments, if pectin is used, the pH in the finished product is about 2.5 to 4.

Furthermore, in some embodiments, various ranges for other properties can assist in the masking of the flavor, such as the water activity (the ratio of the partial pressure of water in the atmosphere in equilibrium with the substrate (e.g. a food) to that of the atmosphere in equilibrium with pure water at the same temperature), brix (the sugar content of an aqueous solution), and levels of acetic acid. In some embodiments, these ranges include a water activity between about 0.3 and 0.85, brix value between about 0.65 and 0.99, and acetic acid levels between about 1% and 50%.

In some embodiments, the nutritional supplement in the present disclosure can have a density of from about 0.6 $g/cm^3$ to 1.4 $g/cm^3$, about 0.7 $g/cm^3$ to 1.3 $g/cm^3$, about 0.8 $g/cm^3$ to 1.2 $g/cm^3$, about 0.9 $g/cm^3$ to 1.1 $g/cm^3$, about 0.8 $g/cm^3$ to 1.0 $g/cm^3$, about 1.0 $g/cm^3$ to 1.2 $g/cm^3$, about 0.9 $g/cm^3$ to 1.2 $g/cm^3$, about 0.7 $g/cm^3$ to 1.1 $g/cm^3$, about 0.85 $g/cm^3$ to 1.15 $g/cm^3$, about 0.95 $g/cm^3$ to 1.05 $g/cm^3$, or about 1.05 $g/cm^3$ to 1.25 $g/cm^3$.

The gel structure of the disclosed nutritional supplement product can be further characterized by textural analysis, such as firmness and resilience (also known as spring back). Firmness and resilience can be measured using a TA.TX texture analyzer (Texture Technologies; Hamilton, Mass.) using conventional methods. Firmness and resilience of the gel structure can be measured in grams force using a TA.TX texture analyzer in compression mode. In some embodiments, the nutritional supplement product can include a gel structure having a firmness measured in grams force of from about 450 g to 1550 g, about 500 g to 1400 g, about 700 g to 1300 g, about 800 g to 1200 g, about 900 g to 1100 g, about 700 g to 1000 g, about 850 g to 1350 g, about 600 g to 900 g, about 550 g to 750 g, or about 925 g to 1275 g.

In some embodiments, the nutritional supplement product can include a gel structure having a resilience of from about 20% to 60% spring back after being held under about 20% compression strain for about one minute. In some embodiments, the nutritional supplement product can include a gel structure having a resilience of from about 25% to 55% spring back, about 35% to 45% spring back, about 30% to 50% spring back, about 20% to 40% spring back, about 40% to 60% spring back, about 30% to 60% spring back, or about 25% to 45% spring back after being held under about 20% compression strain for about one minute. Over the shelf life of the nutritional supplement product, the spring back may be reduced by about 10% to 80%, by about 20% to 70%, by about 30% to 60%, or by about 40% to 50%.

In some embodiments, firmness and/or resilience can be measured at one or more time points during the shelf-life of the nutritional supplement product. In some embodiments, the firmness and/or resilience can be measured at about 0 days to 90 days after production of the nutritional supplement product; at about 1 day to 100 days after production of the nutritional supplement product; or at about 7 days to 80 days after production.

The nutritional supplement product of the present disclosure can be provided in multiple sizes and shapes as desired, including but not limited to, geometric shapes such as a cylinder, sphere, cube, pyramid, and the like; and novelty shapes such as novelty characters, bears, stars, worms, rings fruit, and the like. In some embodiments, the nutritional supplement product can be in the shape of a substantially rounded cylinder, such as a dot form or rounded, truncated cone, or cylinder form. The individual pieces in that embodiment can have a diameter of from about 14 mm to 18 mm, about 12 mm to 20 mm, about 13 mm to 15 mm, or about 15 mm to 18 mm. The individual pieces in that embodiment can have a height of from about 14 mm to 22 mm, about 15 mm to 20 mm, about 16 mm to 18 mm, or about 17 mm to 22 mm. In some embodiments, the weight of an individual piece can be from about 1 gram to 10 grams, about 1 gram to 8 grams, about 1 gram to 6 grams, about 1 gram to 4 grams, about 2 grams to 4 grams, about 2.2 grams to 2.8 grams, about 2.5 grams to 3.5 grams, or about 3 grams to 4 grams. In some embodiments, the weight of an individual piece can be about 4 grams.

Those skilled in the art will recognize, or be able to ascertain, using no more than routine experimentation, numerous equivalents to the specific composition and procedures described herein. Such equivalents are considered to be within the scope of this disclosure, and are covered by the following claims.

The invention claimed is:

1. A food product comprising creatine at about 6% to 35% by weight, a gelling agent, an oligosaccharide, a disaccharide at about 10% to 80% by weight, water, sodium citrate, citric acid, a natural flavor, spirulina, and blueberry, wherein the food product is a gummy.

2. The food product of claim 1, wherein the creatine is selected from the group consisting of creatine monohydrate, creatine hydrochloride, creatine magnesium chelate, pH-buffered creatine, creatine citrate, creatine malate, di-creatine malate, liquid creatine, tri-creatine malate, creatine nitrate, creatine orotate, creatine phosphate, creatine gluconate, creatine pyruvate, creatine alphaketoglutarate, creatine ethyl ester, glycosylated creatine, effervescent creatine, micronized creatine and combinations thereof.

3. The food product of claim 1, wherein the gelling agent is pectin.

4. The food product of claim 1, wherein the oligosaccharide is selected from the group consisting of glucose syrup, corn syrup, rice syrup, invert syrup, isomaltooligosaccharide (IMO) sugar, tapioca, fructooligosaccharide (FOS) syrup, starch, fiber syrup, inulin, fruit puree, fruit concentrate, high maltose syrup, agave syrup, and combinations thereof.

5. The food product of claim 1, wherein the disaccharide is cane sugar.

6. The food product of claim 1, wherein the creatine is by weight between about 7% and 30%.

7. The food product of claim 1, wherein the creatine is by weight between about 8% to 25%.

8. The food product of claim 1, wherein the creatine is by weight between about 12% and 13%.

9. The food product of claim 1, wherein the gelling agent is by weight between about 1% and 20%.

10. The food product of claim 1, wherein the gelling agent is by weight between about 1.75% and 7%.

11. The food product of claim 1, wherein the oligosaccharide is by weight between trace amounts and about 65%.

12. The food product of claim 1, wherein the oligosaccharide is by weight between about 25% and 55%.

13. The food product of claim 1, wherein the disaccharide is by weight between about 10% and 50%.

14. The food product of claim 1, wherein the disaccharide is by weight between about 25% and 70%.

15. The food product of claim 1, wherein the disaccharide is by weight between about 30% and 60%.

* * * * *